(12) United States Patent
Mashimo et al.

(10) Patent No.: US 10,952,968 B2
(45) Date of Patent: Mar. 23, 2021

(54) PREPARATION CONTAINING 6,7-UNSATURATED-7-CARBAMOYL MORPHINAN DERIVATIVES

(71) Applicant: SHIONOGI & CO., LTD., Osaka (JP)

(72) Inventors: Akira Mashimo, Osaka (JP); Shunji Ichio, Osaka (JP); Yoshinori Tamura, Osaka (JP); Kouichi Noguchi, Hyogo (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 14/401,388

(22) PCT Filed: May 13, 2013

(86) PCT No.: PCT/JP2013/063278
§ 371 (c)(1),
(2) Date: Nov. 14, 2014

(87) PCT Pub. No.: WO2013/172297
PCT Pub. Date: Nov. 21, 2013

(65) Prior Publication Data
US 2015/0216804 A1    Aug. 6, 2015

(30) Foreign Application Priority Data
May 14, 2012 (JP) .............................. JP2012-110417

(51) Int. Cl.
*A61K 9/20* (2006.01)
*A61K 9/28* (2006.01)
*A61K 31/485* (2006.01)

(52) U.S. Cl.
CPC .......... *A61K 9/2054* (2013.01); *A61K 9/2009* (2013.01); *A61K 9/2013* (2013.01); *A61K 9/2018* (2013.01); *A61K 9/2027* (2013.01); *A61K 9/2059* (2013.01); *A61K 9/2866* (2013.01); *A61K 31/485* (2013.01)

(58) Field of Classification Search
None
See application file for complete search history.

(56) References Cited

U.S. PATENT DOCUMENTS

| | | | | |
|---|---|---|---|---|
| 4,365,060 | A * | 12/1982 | Onda et al. | 536/65 |
| 4,931,286 | A * | 6/1990 | Johnson | A61K 9/2866 424/480 |
| 5,225,201 | A * | 7/1993 | Beaurline | A61K 31/60 424/464 |
| 6,740,339 | B1 * | 5/2004 | Ohkouchi et al. | 424/464 |
| 9,108,975 | B2 | 8/2015 | Tamura et al. | |
| RE46,365 | E | 4/2017 | Inagaki et al. | |
| 2005/0009811 | A1 | 1/2005 | Albano et al. | |
| 2006/0280789 | A1 * | 12/2006 | Ueki et al. | 424/464 |
| 2009/0203723 | A1 * | 8/2009 | Inagaki et al. | 514/282 |
| 2010/0120815 | A1 | 5/2010 | Takaki et al. | |
| 2010/0215750 | A1 | 8/2010 | Ohta et al. | |
| 2010/0285127 | A1 * | 11/2010 | Barkan | A61K 9/2853 424/480 |
| 2011/0135739 | A1 * | 6/2011 | Carter et al. | 424/489 |
| 2011/0150993 | A1 * | 6/2011 | Zhang | A61K 9/2059 424/464 |
| 2012/0029032 | A1 * | 2/2012 | Fukuda | A61K 9/2009 514/344 |
| 2012/0114752 | A1 | 5/2012 | Ohta et al. | |
| 2013/0231485 | A1 | 9/2013 | Tamura et al. | |

FOREIGN PATENT DOCUMENTS

| | | |
|---|---|---|
| CA | 2 714 524 | 8/2009 |
| EP | 0 747 050 | 12/1996 |
| EP | 1 275 391 | 1/2003 |
| EP | 1 813 274 | 8/2007 |
| EP | 1 889 848 | 2/2008 |
| JP | 2006-306754 | 11/2006 |
| JP | 2010-229075 | 10/2010 |
| JP | 2010-270112 | 12/2010 |
| JP | 2011-105694 | 6/2011 |
| WO | WO 03/000263 | 1/2003 |
| WO | WO 03/020261 | 3/2003 |
| WO | WO 2004/006895 | 1/2004 |
| WO | WO 2006/126637 | 11/2006 |
| WO | 2012/063933 | 5/2012 |

OTHER PUBLICATIONS

Doshi (ibaldi's Drug Delivery Systems in Pharmaceutical Care Ed. Lee et al. Bethesda: American Society of Health-System Pharmacists, Inc., 2007, p. 23-30.*
Gennaro et al. Remington's Pharmaceutical Sciences Easton: Mack Publishing Company, 1985, p. 1280.*
Lactose MSDS 2 pages (Year: 2009).*
Juhl et al. Journal of Pharmaceutical Sciences 1973 62(1): 170 (Year: 1973).*
Ingram et al. Journal of Pharmaceutical Sciences 1966 55(5):614-617 (Year: 1966).*
Rao et al. International Journal of Pharmaceutical Sciences and Research 2010 1(4):56-66 (Year: 2010).*
15th Edition of the Japanese Pharmacopeia 2006 p. 116-119 (Year: 2006).*

(Continued)

*Primary Examiner* — Robert A Wax
*Assistant Examiner* — Caralynne E Helm
(74) *Attorney, Agent, or Firm* — Wenderoth, Lind & Ponack, L.L.P.

(57) ABSTRACT

The solid preparation which improved the dissolution profile and the stability of the 6,7-unsaturation-7-carbamoyl morphinan derivative is provided. When 6,7-unsaturation-7-carbamoyl morphinan derivative, croscarmellose sodium and ferric oxide were contained, not titanium oxide in the solid preparations and the coating solid preparations, a dissolution rate after 15 minutes of the dissolution test is more than 85%, and stability, particularly, light stability can be improve.

13 Claims, 2 Drawing Sheets

(56) References Cited

OTHER PUBLICATIONS

Notification of Transmittal of Translation of the International Preliminary Report on Patentability, International Preliminary Report on Patentability, and Translation of the Written Opinion of the International Searching Authority, for International Patent Application No. PCT/JP2013/063278, dated Nov. 27, 2014 (10 pages).
English-language International Search Report from the Japanese Patent Office for International Application No. PCT/JP2013/063278, dated Jul. 9, 2013.

* cited by examiner

PREPARATION CONTAINING 6,7-UNSATURATED-7-CARBAMOYL MORPHINAN DERIVATIVES

TECHNICAL FIELD

The present invention relates to a preparation containing 6,7-unsaturated-7-carbamoyl morphinan derivatives, especially, which improve dissolution profile and stability of 17-(cyclopropylmethyl)-6,7-didehydro-4,5α-epoxy-3,6,14-trihydroxy-N-[2-(3-phenyl-1,2,4-oxadiazol-5-yl)propan-2-yl]morphinan-7-carboxamide 4-methylbenzenesulfonic acid.

BACKGROUND ART

An agonist on opioid receptor, such as morphine, is used as very effective analgesic, but it induces the strong nausea, retching, constipation, ischuria, itch and the like as side effects. The various antiemetic and anti-constipation is used clinically. However, all of them do not exhibit a sufficient effect, and an agent excellently reducing an adverse effect is requested to improve QOL of patients.

Patent Publication 1 describes 6,7-unsaturated-7-carbamoyl morphinan derivatives (hereinafter, also referred to as "present derivative") as the agent reducing an adverse effect. With respect to the solid preparation containing the present derivative, especially, 17-(cyclopropylmethyl)-6,7-didehydro-4,5α-epoxy-3,6,14-trihydroxy-N-[2-(3-phenyl-1,2,4-oxadiazol-5-yl)propan-2-yl]morphinan-7-carboxamide 4-methyl benzenesulfonic acid (Compound A, hereinafter, also referred to as "present compound"), which is effective as the above agent reducing an adverse effect, the efficacy of drug may decrease, depending on the additive agent, when the dissolution profile, especially, the dissolution rate on the early stage after the beginning of dissolution test is low. Moreover, a pigment should be added in order to distinguish the preparation, but it threatens to decrease the temporal stability and the light stability. On the preparation containing the compound other than the present derivatives, the improvement of the dissolution profile (Patent Publication 2-6) and the improvement of the stability of compound (Patent Publication 7-12) are disclosed. However, the chemical structure between the compound in the above publication and 6,7-unsaturated-7-carbamoyl morphinan derivatives is very different, and the preparation in the above publication does not always improve the dissolution profile and the stability of the present derivatives.

PRIOR ART

Patent Publication

[Patent Publication 1] International Publication brochure of WO 2006/126637
[Patent Publication 2] JP-A No. 8-333253
[Patent Publication 3] JP-A No. 2009-501694
[Patent Publication 4] International Publication brochure of WO 2009/101940
[Patent Publication 5] JP-A No. 2004-521146
[Patent Publication 6] JP-A No. 2009-501694
[Patent Publication 7] JP-A No. 2005-520785
[Patent Publication 8] JP-A No. 2005-535671
[Patent Publication 9] JP-A No. 2006-306754
[Patent Publication 10] JP-A No. 2011-105694
[Patent Publication 11] JP-A No. 2010-229075
[Patent Publication 12] International Publication brochure of WO 2006/38661

DISCLOSURE OF INVENTION

Problems to be Solved by the Invention

Therefore, the development of a preparation having improved the dissolution profile of the present derivatives or the present compound, especially the dissolution rate in the early stage, and the temporal stability and the light stability, and having discrimination has been demanded.

Means to Solve the Problems

The present inventors intensively studied, and found out that dissolution profile and stability can be improved by optional additive agents in a preparation containing the present derivative and the present compound. That is, by using croscarmellose sodium or crospovidone as a disintegrator, and without using titanium oxide as a pigment, by using a pigment such as ferric oxide, tar dye, natural dye and the like, the formulation improving the dissolution profile and the stability and having discrimination can be manufactured.

That is, the present invention related to:

(1) a solid preparation comprising a pharmaceutically acceptable salt of a compound represented by formula (IA) or a solvate of the compound or the salt as an active ingredient:

[Chemical formula 1]

(IA)

(2) the solid preparation according to above (1), which contains the salt of the compound represented by formula (IA) or the solvate of the compound or the salt as the active ingredient, and a disintegrator, (3) the solid preparation, which contains the compound represented by formula (IA), its pharmaceutically acceptable salt, or a solvate thereof as an active ingredient, and the disintegrator, wherein the dissolution rate of the compound represented by formula (IA) is more than 85% after 15 minutes of the test initiation in the second method (the paddle method) of dissolution test regulated in the 15$^{th}$ revised Japanese Pharmacopoeia, (4) the solid preparation, which contains the compound represented by formula (IA), its pharmaceutically acceptable salt, or a solvate thereof as an active ingredient, and the disintegrator, wherein the amount of relative substances of the compound represented by formula (IA) is less than 0.2% under 40° C., the relative humidity of 75% for one month's preservation, (5) the solid preparation according to the above (3) or (4), which contains the compound represented by formula (IA), its pharmaceutically acceptable salt, or a solvate thereof as the active ingredient, and the disintegrator, wherein the dissolution rate of the compound represented by formula (IA) is more than 85% after 15 minutes of the test initiation in the second liquid of dissolution test regulated in the Japanese Pharmacopoeia, and the amount of relative substances of the compound represented by formula (IA) is less than 0.2% under 40° C., the relative humidity of 75% for one month's preservation, (6) the solid preparation according to any one of the above (1) to (5), wherein the active ingredient is p-toluenesulfonic acid salt, acetate or hydrochloride salt of the compound represented by formula (IA), or a solvate of the salt, (7) the solid preparation according to any one of the above (1) to (6), wherein the disintegrator is one or more selected from the group consisting of cellulose type disintegrator, starch type disintegrator and vinyl type disintegrator, (8) the solid preparation according to the above (7), wherein the disintegrator is cellulose type disintegrator, (9) the solid preparation according to the above (8), wherein the cellulose type disintegrator is sodium salt, (10) the solid preparation according to the above (8), wherein the cellulose type disintegrator is croscarmellose sodium, (11) the solid preparation according to the above (7), wherein the disintegrator is vinyl type disintegrator, (12) the solid preparation according to above the (11), wherein the vinyl type disintegrator is crospovidone, (13) the solid preparation according to any one of the above (6) to (12) containing 0.25 to 250 parts by weight of disintegrator based on 1 parts by weight of the active ingredient, which is p-toluenesulfonic acid salt, acetate or hydrochloride salt of the compound represented by formula (IA), or a solvate of the salt, (14) the solid preparation according to any one of the above (1) to (13), which contains one or more selected from the group consisting of ferric oxide, tar dye and natural dye, and does not substantially contain titanium oxide, (15) the solid preparation according to any one of the above (1) to (13), which contains ferric oxide, and does not substantially contain titanium oxide, (16) the coating solid preparation, wherein the coating layer is formed on the surface of the solid preparation according to any one of above the (1) to (15), (17) the solid preparation according to the above (16), which contains one or more selected from the group consisting of ferric oxide, tar dye and natural dye and does not substantially contain titanium oxide in the coating layer, (18) the solid preparation according to the above (16), which contains ferric oxide and does not substantially contain titanium oxide in the coating layer, (19) the coating solid preparation according to the above (18), wherein the coating layer is formed on the surface of the solid preparation which contains p-toluenesulfonic acid salt, acetate or hydrochloride salt of the compound represented by formula (IA), or a solvate of the salt and croscarmellose sodium, which contains ferric oxide and does not substantially contain titanium oxide in the coating layer, (20) the solid preparation, which contains p-toluenesulfonic acid salt, acetate or hydrochloride salt of the compound represented by formula (IA), or a solvate of the salt, and contains one or more selected from the group consisting of ferric oxide, tar dye and natural dye and does not substantially contain titanium oxide, (21) the coating solid preparation, wherein the coating layer is formed on the surface of the solid preparation which contains p-toluenesulfonic acid salt, acetate or hydrochloride salt of the compound represented by formula (IA), or a solvate of the salt, which contains one or more selected from the group consisting of ferric oxide, tar dye and natural dye and does not substantially contain titanium oxide in the coating layer, (22) the solid preparation or the coating solid preparation according to any one of the above (14) to (21), wherein the ferric oxide is iron sesquioxide and/or yellow iron sesquioxide, (23) the solid preparation or the coating solid preparation according to any one of the above (1) to (22), wherein the preparation is a tablet or a granule.

Effect of the Invention

When the preparation containing 6,7-unsaturated-7-carbamoyl morphinan derivatives of the present invention contains croscarmellose sodium or crospovidone in the preparation, the dissolution rate of the compound represented by formula (IA) can be more than 85% in early stage of the dissolution test, especially after 15 minutes of the initiation of the dissolution test. Moreover, without using titanium dioxide as a pigment, by using a pigment such as ferric oxide, tar dye, natural dye and the like, the formulation improving the dissolution profile and the stability and having discrimination can be manufactured.

BEST MODE FOR CARRYING OUT THE INVENTION

The agent for reducing an adverse effect induced by the compound having the opioid receptor agonistic activity is usually 6,7-unsaturated-7-carbamoyl-substituted morphinan derivatives, preferably the compound represented by the above formula (IA) (compound A), a pharmaceutically acceptable salt of the compound, or a solvate thereof, more preferably a pharmaceutically acceptable salt of the compound represented by the above formula (IA), or a solvate of the compound or the salt.

Examples of a pharmaceutically acceptable salt of the compound (IA) include salts with alkali metals (for example lithium, sodium, potassium and the like), alkaline earth metals (for example calcium, barium and the like), magnesium, transition metals (for example zinc, iron and the like) ammonia, organic bases (for example trimethylamine, triethylamine, dicyclohexylamine, ethanolamine, diethanolamine, triethanolamine, meglumine, diethanolamine, ethylenediamine, pyridine, picoline, quinolone and the like), and amino acid, or salts with inorganic acids (for example hydrochloric acid, sulfuric acid, nitric acid, carbonic acid, hydrobromic acid, phosphoric acid and hydroiodic acid and the like) and organic acids (for example formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid and the like). Particularly, examples of salts include hydrochloric acid, phosphoric acid, tartaric acid, or methanesulfonic acid. Preferable is salts with acid. These salts can be formed by a conventional method.

Examples of salts include particularly preferably p-toluenesulfonic acid salt, acetate or hydrochloride salt of the compound represented by the above formula (IA), or a solvate of the compound or the salt, more preferably a crystal of p-toluenesulfonic acid salt of the compound represented by the above formula (IA), or the crystal of the solvate of the salt, especially preferably 17-(cyclopropylmethyl)-6,7-didehydro-4,5α-epoxy-3,6,14-trihydroxy-N-[2-(3-phenyl-1,2,4-oxadiazol-5-yl)propan-2-yl]morphinan-7-carboxamide 4-methylbenzenesulfonic acid.

The crystal of p-toluenesulfonic acid of the compound (Compound A) represented by the above formula (IA) does not have the humidity and have the excellent stability. In addition, the crystal exists in a state of crystal in the solid preparation. The present compound, the manufacturing method of the crystal of the compound, properties of thereof and the like is described in claims and descriptions in international publication brochures of WO 2006/126637 and WO2012/063933.

The water solubility of p-toluenesulfonic acid salt of the compound represented by the above formula (IA), namely 17-(cyclopropylmethyl)-6,7-didehydro-4,5α-epoxy-3,6,14-trihydroxy-N-[2-(3-phenyl-1,2,4-oxadiazol-5-yl) propan-2-yl]morphinan-7-carboxamide 4-methylbenzene sulfonic acid is more than 1,000 µg/mL in pH 1 or 4, but the water solubility in pH 7 decreases than the solubility in pH 1 or 4.

A content of the p-toluenesulfonic acid salt, acetate or hydrochloride salt of the compound represented by the above formula (IA), or the solvate of the present compound or the salt, especially the content of present compound may be preferably an amount at which the drug efficacy is obtained. For example, the content is 0.01 to 20% by weight, preferably 0.025 to 17.5 by weight, more preferably 0.05 to 15 by weight based on a total amount of the preparation. When the content is more than these amounts, there is a possibility that tablet cannot be formed and, when the content is less than these amounts, there is a possibility that the decomposed amount of active ingredient is greater.

The present preparation may contain a disintegrator, those described in Japanese Pharmacopoeia, Pharmaceutical Standards outside the Japanese Pharmacopoeia, Japanese Pharmaceutical Excipients and Japanese Standard of Food Additives may be used, and examples include cellulose type disintegrator, starch type disintegrator and vinyl type disintegrator. Examples of cellulose type disintegrator include croscarmellose sodium, carmellose sodium, carmellose calcium, carmellose, crystalline cellulose, crystalline cellulose•carmellose sodium, low substituted hydroxypropylcellulose, hydroxyethylcellulose, hydroxypropylcellulose, hydroxypropylmethylcellulose and the like. Examples of starch type disintegrator include carboxymethylstarch sodium, hydroxypropylstarch, corn starch, wheat starch, potato starch, pregelatinized starch, partly pregelatinized starch and the like. Examples of vinyl type disintegrator include polyvinylpyrrolidone, crospovidone and the like. Preferably is cellulose type disintegrator and vinyl type disintegrator, in the case of cellulose type disintegrator, more preferably croscarmellose sodium, carmellose sodium, crystalline cellulose•carmellose sodium, especially preferable croscarmellose sodium.

A content of the disintegrator is the 0.25 to 250 parts by weight of disintegrator based on the 1 part by weight of present compound, especially p-toluenesulfonic acid salt, acetate and hydrochloride salt of compound represented by formula (IA), or the solvate of the present compound, or the salt, preferably 0.375 to 225 parts by weight, more preferably, from 0.5 to 200 parts by weight. A content of the disintegrator is usually from 1 to 30% by weight preferably from 2.5 to 25% by weight, more preferably from 5 to 20% by weight per the preparation. When a content is larger than this content, there is a possibility that a preparation becomes larger. When a content is smaller than this content, there is a possibility that a preparation does not exhibit particularly good disintegration or dissolution of the preparations.

As the dissolution profile usually influences on the absorption of the drug, it is preferable for dissolution profiles in the early stage of the dissolution test to become high. The dissolution profile on the early stage of dissolution test is affected by a disintegrator. For example, when the dissolution test in the second method (the paddle method) of dissolution test in the 15th revised Japanese Pharmacopoeia of preparation before coating of coating agent (hereinafter, also referred to as "solid preparation") is conducted, 1) the dissolution rate of compound represented by formula (IA) is usually more than 85% after 15 minutes of dissolution test, preferably more than 87.5%, more preferably more than 90%, 2) the dissolution rate of compound represented by formula (IA) is usually more than 60% after 5 minutes of dissolution test, preferably more than 62.5%, more preferably more than 65%, and the dissolution rate of compound represented by formula (IA) is usually more than 85% after 15 minutes of dissolution test, preferably more than 87.5%, more preferably more than 90%, 3) the dissolution rate of compound represented by formula (IA) is usually more than 60% after 5 minutes of dissolution test, preferably more than 62.5%, more preferably more than 65%, and the dissolution rate of compound represented by formula (IA) is usually more than 85% after 15 minutes of dissolution test, preferably more than 87.5%, more preferably more than 90%, and the dissolution rate of compound represented by formula (IA) is usually more than 90% after 30 minutes of dissolution test, preferably more than 92.5%, more preferably more than 95%, 4) the dissolution rate of compound represented by formula (IA) is usually more than 85% after 15 minutes of dissolution test, preferably more than 87.5%, more preferably more than 90%, and the dissolution rate of compound represented by formula (IA) is usually more than 90% after 30 minutes of dissolution test, preferably more than 92.5%, more preferably more than 95%.

The disintegration on the preparation of the present invention is affected by disintegrator very much, and the disintegration may be suitable for absorption of the present compound in vivo. When the disintegration test of the general method in the 15$^{th}$ revised Japanese Pharmacopoeia of the solid preparation in the present invention is conducted, the disintegration time is usually not more than 120 seconds, preferably not more than 115 seconds, more preferably not more than 110 seconds.

The relative substance of present compound on the preparation of the present invention is affected highly by the disintegrator. There is a hydroxide of compound represented by formula (IA) as main relative substance. For example, when the solid preparation is preserved under 40° C., 75% relative humidity for a month, the sum of all relative substance to the present compound (hereinafter, also referred to as "all relative substance") is usually less than 0.3%, preferably less than 0.25%, more preferably less than 0.2%. When the content of relative substance is larger than this content, there is a possibility that the toxicity might occur.

The preparation may contain an excipient, those described in Japanese Pharmacopoeia, Pharmaceutical Standards outside the Japanese Pharmacopoeia, Japanese Pharmaceutical Excipients and Japanese Standard of Food Additives may be used, a preferable excipient may be an excipient which can be tableted directly. Examples of excipient include D-mannitol, powdered hydrogenated maltose starch syrup, glucose, fructose, lactose, erythritol, maltitol, trehalose, sorbitol, sucrose, saccharose, fructo-oligosaccharide, palatinose, maltose (maltose), hydrogenated maltose starch, powdered syrup, starch syrup, fructose, lactulose, hydrogenated lactose lactitol, honey sugar, D-sorbitol, xylitol, corn starch, potato starch, wheat starch, rice starch, crystal cellulose, silicic anhydride, anhydrous calcium phosphate, precipitated calcium carbonate, calcium silicate and the like. Preferably is D-mannitol.

A content of the excipient is usually 50 to 95% by weight, preferably from 60 to 92.5% by weight, more preferably from 70 to 90% by weight per preparation. When a content is larger than these contents, there is a possibility that a preparation in itself may upsize. When a content is smaller than this content, the tablet cannot be formed.

The preparation may contain a lubricant, those described in Japanese Pharmacopoeia, Pharmaceutical Standards outside the Japanese Pharmacopoeia, Japanese Pharmaceutical Excipients and Japanese Standard of Food Additives may be used. Examples of lubricant include stearate metal salt, sucrose fatty acid ester, talc, hydrated silicon dioxide and the like, but preferably is stearate metal salt. Examples of stearate metal salts include magnesium stearate, calcium stearate, but preferably is magnesium stearate.

A content of the lubricant is usually 0.05 to 10% by weight, preferably 0.075 to 7.5% by weight, more preferably 0.1 to 5% by weight per preparation. When a content is larger than this content, there is a possibility that a dissolution profile of preparation become low. When a content is smaller than this content, there is a possibility that a tablet cannot be formed.

The present preparation may contain a pigment or a color agent, those described in Japanese Pharmacopoeia, Pharmaceutical Standards outside the Japanese Pharmacopoeia, Japanese Pharmaceutics Excipients and Japanese Standard of Food Additives may be used. Examples of a pigment or a color agent include ferric oxide, tar dye, natural dye and the like. Examples of ferric oxide include red ferric oxide, yellow oxide of iron, yellow ferric oxide, black oxide of iron and the like. Examples of tar dye include Food Yellow No. 4 aluminum lake, Food Blue No. 1 aluminum lake, Food Red No. 3 aluminum lake, Food blue No. 1, Food blue No. 2, Food yellow No. 4, Food yellow No. 5, Food red No. 102, Food red No. 2, Food red No. 3 and the like. Examples of natural pigment include rye green leaf extract at Turmeric extract, β-carotine, carotine liquid, copper chlorophyllin sodium, copper chlorophyll, a rye green leaf extract end, a rye green leaf extract end dry powder, a rye green leaf extract end and the like. However, it is desirable not to contain the pigment which decomposes the present compound, especially p-toluenesulfonic acid salt, acetate, hydrochloride salt of a compound represented by formula (IA), or the present compound, or a solvate thereof under the temporal stability during storage or photon irradiation. For example, when the light is irradiated to the preparation containing the present compound and titanium oxide, the amount of relative substances of the compound increases. Therefore it is desirable not to contain titanium oxide in the preparation substantially. "not contain titanium oxide substantially" means that the amount of titanium oxide per preparation is less than 0.001% by weight.

When ultraviolet is irradiated to titanium oxide which usually is used as a pigment, free radical generates in the presence of water and oxygen. This free radical has high oxidizability and oxidants of the compound may optionally arise. Since it is presumed that the relative substance compound of the present compound increases by free radical, a pigment which does not generate free radical is selected.

A content of the pigment or color agent is usually 0.001 to 1 parts by weight based on the present compound, especially p-toluenesulfonic acid salt, acetate, or hydrochloride salt of the 1 part by weight of compound represented by formula (IA), or the solvate of the present compound, or the salt, preferably 0.0025 to 0.75 parts by weight, more preferably 0.05 to 0.5 parts by weight. A content of the pigment or color agent is usually 0.001 to 2% by weight, preferably 0.0025 to 1.5% by weight, more preferably 0.005 to 1% by weight per preparation.

The present preparation may coat the coating agent on the surface of the preparation, those described in Japanese Pharmacopoeia, Pharmaceutical Standards outside the Japanese Pharmacopoeia, Japanese Pharmaceutical Excipients and Japanese Standard of Food Additives may be used. Examples of a coating agent include hypromellose (hydroxypropyl methylcellulose), polyvinyl alcohol, ethyl cellulose, carboxymethylethylcellulose, carmellose, carmellose sodium, hydroxyethylcellulose, hydroxyethylmethylcellulose, hydroxypropylcellulose, PVA copolymer, acrylic acid ethyl•methyl methacrylate copolymer dispersion liquid, amino alkyl methacrylate copolymer, opadry, carnabaro, carboxy vinyl polymers, dry methacrylate copolymer, dimethylamino ethyl methacrylate•methyl methacrylate copolymer, stearyl alcohol, shellac, cetanol, hydroxypropylmethylcellulose acetate succinate, hydroxypropylmethylcellulose phthalate, fumarate•stearic acid, •polyvinyl acetal diethylamino acetate•hydroxypropyl methylcellulose mixture, polyvinyl acetal diethylamino acetate, polyvinyl alcohol, methacrylate copolymer, 2-methyl-5-vinyl pyridine methyl acrylate•methacrylic acid copolymer and the like, preferably hypromellose (hydroxypropyl methylcellulose). In the present specifications, the preparation after coating the coating agent refers to "the coating solid preparation", the layer which coated the coating agent refers to "the coating layer".

A content of the coating agent is usually 0.1 to 10% by weight, preferably 0.25 to 7.5% by weight, more preferably 0.5 to 5% by weight per preparation. When a content is larger than this content, there is a possibility that a dissolution rate of preparation become low. When a content is smaller than this content, there is a possibility that a coating membrane is damaged.

A pigment or the coloring agent may be contained in the solid preparation, but may be contained in the solid preparation of the coating solid preparation and/or coating layer.

To conduct coating process effectively, the preparation may contain a plasticizer or a dispersing agent in the coating agent, those described in Japanese Pharmacopoeia, Pharmaceutical Standards outside the Japanese Pharmacopoeia, Japanese Pharmaceutical Excipients and Japanese Standard of Food Additives may be used. Examples of a plasticizer or a dispersing agent include macrogol such as macrogol 1000, macrogol 1500, macrogol 1540, macrogol 4000, macrogol 6000, macrogol 8000, macrogol 20000, macrogol 35000 (polyethylene glycol of average molecular weight 1000-35,000) and the like, fatty acid ester of glycerin, sucrose fatty acid ester, castor oil and talc and the like. But it is desirable not to contain a plasticizer or a dispersing agent, which decompose the present derivative, in particular, p-toluenesulfonic acid salt, acetate and hydrochloride salt of the compound represented by formula (IA), or the present compound, or a solvate thereof of acid addition salt, especially the present compound. For example, it is desirable not to contain a sodium citrate substantially in this preparation. "not to contain a sodium citrate substantially" means that the amount of sodium citrate is less than 0.001% by weight per preparation.

The preparation may contain an additive agent except those mentioned above, if necessary, those described in Japanese Pharmacopoeia, Pharmaceutical Standards outside the Japanese Pharmacopoeia, Japanese Pharmaceutical Excipients and Japanese Standard of Food Additives may be used. Moreover, the content of these additive agents may be a certain ratio. Examples of additive agent except those mentioned above include the binding agent, perfume, fluidity agent, taste masking agent and the like.

Examples of a binding agent include hydroxypropylcellulose, corn starch, pregelatinized starch, partly pregelatinized starch, acacia, powdered acacia, gelatin, agar, dextrin, pullulan, polyvinylpyrrolidone, polyvinyl alcohol, crystal cellulose, methylcellulose, ethylcellulose, carboxymethylethylcellulose, carmellose, carmellose sodium, hydroxyethyl cellulose, hydroxyethylmethylcellulose, hydroxypropylcellulose, hypromellose and the like.

Examples of perfume include orange extract, orange oil, caramel, camphor, cinnamon bark oil, spearmint oil, strawberry extract, chocolate extract, cherry flavor, sour orange oil, pine oil, mentha oil, vanilla flavor, bitter extract, fruit flavor, peppermint extract, mixture flavor, mint flavor, menthol, lemon powder, lemon oil, rose oil and the like.

Examples of fluidity agent include hydrated silicon dioxide, light anhydrous silicic acid, crystal cellulose, synthetic aluminum silicate, talc and the like.

Examples of taste masking agent include aspartame, sucralose, glycine, sodium chloride, magnesium chloride, hydrochloric acid, dilute hydrochloric acid, citric acid and the salt, anhydrous citric acid, L-glutaminic acid and the salt, succinic acid and the salt, acetic acid, tartaric acid and the salt, sodium hydrogen carbonate, fumaric acid and the salt, malic acid and the salt, glacial acetic acid, inosinic acid disodium, honey and the like.

When the above active ingredient and the additive agent is not in the range of decreasing the dissolution profile of an active ingredient and stability, the optional amount can be used alone or mixture. In the solid preparation, the combination of preferably active ingredient and additives are 1) present compound/croscarmellose sodium or crospovidone, 2) present compound/croscarmellose sodium or crospovidone/ferric oxide, 3) present compound/croscarmellose sodium or crospovidone/ferric oxide/mannitol, 4) present compound/croscarmellose sodium or crospovidone/ferric oxide/mannitol/magnesium stearate, 5) present compound/croscarmellose sodium or crospovidone/mannitol, 6) present compound/croscarmellose sodium or crospovidone/mannitol/magnesium stearate. Any above combination does not contain titanium oxide. In the coating solid preparation, the combination of an active ingredient and an additive agent is above 1)~4) on the part of solid preparation, and the combination is 1) hypromellose, 2) hypromellose/ferric oxide on the part of coating layer, and in any combinations, titanium oxide is not contained substantially in the preparation.

When the solid preparation is a combination of present compound/croscarmellose sodium or crospovidone, the content of croscarmellose sodium or crospovidone is 0.25 to 250 parts by weight, preferably 0.375 to 225 parts by weight, and more preferably 0.5 to 200 parts by weight based on 1 part by weight of the present compound. Moreover, each content per preparation is such that, usually, present compound is 0.01 to 20% by weight, croscarmellose sodium or crospovidone is 1 to 30% by weight, preferably, present compound is 0.025 to 17.5% by weight, croscarmellose sodium or crospovidone is 2.5 to 25% by weight, more preferably, present derivative is 0.05 to 15% by weight, croscarmellose sodium or crospovidone is 5 to 20% by weight, and titanium oxide is not contained substantially in the preparation.

When the solid preparation is a combination of present compound/croscarmellose sodium or crospovidone/ferric oxide, the content of croscarmellose sodium or crospovidone is 0.25 to 250 parts by weight, preferably 0.375 to 225 parts by weight, and more preferably 0.5 to 200 parts by weight, the content of ferric oxide is usually 0.001 to 1 parts by weight, preferably 0.0025 to 0.75 parts by weight, and more preferably 0.05 to 0.5 parts by weight based on 1 part by weight of the present compound. Moreover, each content per preparation is such that, usually, present compound is 0.01 to 20% by weight, croscarmellose sodium or crospovidone is 1 to 30% by weight, ferric oxide is 0.001 to 2% by weight, preferably, present compound is 0.025 to 17.5% by weight, croscarmellose sodium or crospovidone is 2.5 to 25% by weight, ferric oxide is 0.0025 to 1.5% by weight, more preferably, present compound is 0.05 to 15% by weight, croscarmellose sodium or crospovidone is 5 to 20% by weight, ferric oxide is 0.005 to 1% by weight, and titanium oxide is not contained practically in the preparation.

When the solid preparation is a combination of present compound/croscarmellose sodium or crospovidone/ferric oxide/mannitol, the content of croscarmellose sodium or crospovidone, ferric oxide based on 1 part by weight of the present compound is as mentioned above. Moreover, each content per preparation is such that, usually, present compound is 0.01 to 20% by weight, croscarmellose sodium or crospovidone is 1 to 30% by weight, ferric oxide is 0.001 to 2% by weight, mannitol is 50 to 95% by weight, preferably, present compound is 0.025 to 17.5% by weight, croscarmellose sodium or crospovidone is 2.5 to 25% by weight, ferric oxide is 0.0025 to 1.5% by weight, mannitol is 60 to 92.5% by weight, more preferably, present compound is 0.05 to 15% by weight, croscarmellose sodium or crospovidone is 5 to 20% by weight, ferric oxide is 0.005 to 1% by weight, mannitol is 70 to 90% by weight, and titanium oxide is not contained substantially in the preparation.

When the solid preparation is a combination of present compound/croscarmellose sodium or crospovidone/ferric oxide/mannitol/magnesium stearate, the content of croscarmellose sodium or crospovidone, ferric oxide based on 1 part by weight of the present compound is as mentioned above. Moreover, each content per preparation is such that, usually, present compound is 0.01 to 20% by weight, croscarmellose sodium or crospovidone is 1 to 30% by weight, ferric oxide is 0.001 to 2% by weight, mannitol is 50 to 95% by weight, magnesium stearate is 0.05 to 10% by weight, preferably, present compound is 0.025 to 17.5% by weight, croscarmellose sodium or crospovidone is 2.5 to 25% by weight, ferric oxide is 0.0025 to 1.5% by weight, mannitol is 60 to 92.5% by weight, magnesium stearate is 0.075 to 7.5% by weight, more preferably, present compound is 0.05 to 15% by weight, croscarmellose sodium or crospovidone is 5 to 20% by weight, ferric oxide is 0.005 to 1% by weight, mannitol is 70 to 90% by weight, magnesium stearate is 0.1 to 5% by weight, and titanium oxide is not contained substantially in the preparation.

When the solid preparation is a combination of present compound croscarmellose sodium or crospovidone and the coating solid preparation wherein the coating layer, which is coated on the surface of solid preparation, is hypromellose, the content of croscarmellose sodium or crospovidone based on 1 part by weight of the present compound is as mentioned above. Moreover, each content per preparation is such that, usually present compound is 0.01 to 20% by weight, croscarmellose sodium or crospovidone is 1 to 30% by weight, hypromellose is 0.1 to 10% by weight, preferably, present compound is 0.025 to 17.5% by weight, croscarmellose sodium or crospovidone is 2.5 to 25% by weight, hypromellose is 0.25 to 7.5% by weight, more preferably, present compound is 0.05 to 15% by weight, croscarmellose sodium or crospovidone is 5 to 20% by weight, hypromellose is 0.5 to 5% by weight, and titanium oxide is not contained substantially in the preparation.

When the solid preparation is a combination of present compound/croscarmellose sodium or crospovidone/ferric oxide and the coating solid preparation wherein the coating layer, which is coated on the surface of solid preparation, is hypromellose, the content of croscarmellose sodium or crospovidone, ferric oxide based on 1 part by weight of the present compound is as mentioned above. Moreover, each content per preparation is such that, usually, present compound is 0.01 to 20% by weight, croscarmellose sodium or crospovidone is 1 to 30% by weight, ferric oxide is 0.001 to 2% by weight, hypromellose is 0.1 to 10% by weight, preferably, present compound is 0.025 to 17.5% by weight, croscarmellose sodium or crospovidone is 2.5 to 25% by weight, ferric oxide is 0.0025 to 1.5% by weight, hypromellose is 0.25 to 7.5% by weight, more preferably, present compound is 0.05 to 15% by weight, croscarmellose sodium or crospovidone is 5 to 20% by weight, ferric oxide is 0.005 to 1% by weight, hypromellose is 0.5 to 5% by weight, and titanium oxide is not contained substantially in the preparation.

When the solid preparation is a combination of present compound/croscarmellose sodium or crospovidone/ferric oxide/mannitol and the coating solid preparation wherein the coating layer, which is coated on the surface of solid preparation, is hypromellose, the content of croscarmellose sodium or crospovidone, ferric oxide based on 1 part by weight of the present compound is as mentioned above. Moreover, each content per preparation is such that, usually, present compound is 0.01 to 20% by weight, croscarmellose sodium or crospovidone is 1 to 30% by weight, ferric oxide is 0.001 to 2% by weight, mannitol is 50 to 95% by weight, hypromellose is 0.1 to 10% by weight, preferably, present compound is 0.025 to 17.5% by weight, croscarmellose sodium or crospovidone is 2.5 to 25% by weight, ferric oxide is 0.0025 to 1.5% by weight, mannitol is 60 to 92.5% by weight, hypromellose is 0.25 to 7.5% by weight, more preferably, present compound is 0.05 to 15% by weight, croscarmellose sodium or crospovidone is 5 to 20% by weight, ferric oxide is 0.005 to 1% by weight, mannitol is 70 to 90% by weight, hypromellose is 0.5 to 5% by weight, and titanium oxide is not contained substantially in the preparation.

When the solid preparation is a combination of present compound/croscarmellose sodium or crospovidone/ferric oxide/mannitol/magnesium stearate and the coating solid preparation wherein the coating layer, which is coated on the surface of solid preparation, is hypromellose, the content of croscarmellose sodium or crospovidone, ferric oxide based on 1 part by weight of the present compound is as mentioned above. Moreover, each content per preparation is such that, usually, present compound is 0.01 to 20% by weight, croscarmellose sodium or crospovidone is 1 to 30% by weight, ferric oxide is 0.001 to 2% by weight, mannitol is 50 to 95% by weight, magnesium stearate is 0.05 to 10% by weight, hypromellose is 0.1 to 10% by weight, preferably, present compound is 0.025 to 17.5% by weight, croscarmellose sodium or crospovidone is 2.5 to 25% by weight, ferric oxide is 0.0025 to 1.5% by weight, mannitol is 60 to 92.5% by weight, magnesium stearate is 0.075 to 7.5% by weight, hypromellose is 0.25 to 7.5% by weight, more preferably, present compound is 0.05 to 15% by weight, croscarmellose sodium or crospovidone is 5 to 20% by weight, ferric oxide is 0.005 to 1% by weight, mannitol is 70 to 90% by weight, magnesium stearate is 0.1 to 5% by weight, hypromellose is 0.5 to 5% by weight, and titanium oxide is not contained substantially in the preparation.

When the solid preparation is a combination of present compound/croscarmellose sodium or crospovidone/ferric oxide and the coating solid preparation wherein the coating layer, which is coated on the surface of solid preparation, is hypromellose/ferric oxide, the content of croscarmellose sodium or crospovidone, ferric oxide based on 1 part by weight of the present compound is as mentioned above. Moreover, each content per preparation is such that, usually, present compound is 0.01 to 20% by weight, croscarmellose sodium or crospovidone is 1 to 30% by weight, hypromellose is 0.1 to 10% by weight, ferric oxide is 0.001 to 2% by weight, preferably, present compound is 0.025 to 17.5% by weight, croscarmellose sodium or crospovidone is 2.5 to 25% by weight, hypromellose is 0.25 to 7.5% by weight, ferric oxide is 0.0025 to 1.5% by weight, more preferably, present compound is 0.05 to 15% by weight, croscarmellose sodium or crospovidone is 5 to 20% by weight, hypromellose is 0.5 to 5% by weight, ferric oxide is 0.005 to 1% by weight, and titanium oxide is not contained substantially in the preparation.

When the solid preparation is a combination of present compound/croscarmellose sodium or crospovidone/ferric oxide and the coating solid preparation wherein the coating layer, which is coated on the surface of solid preparation, is hypromellose/ferric oxide, the content of croscarmellose sodium or crospovidone, ferric oxide based on 1 part by weight of the present compound is as mentioned above. Moreover, each content per preparation is such that, usually, present compound is 0.01 to 20% by weight, croscarmellose sodium or crospovidone is 1 to 30% by weight, ferric oxide is 0.001 to 2% by weight, hypromellose is 0.1 to 10% by weight, preferably present compound is 0.025 to 17.5% by weight, croscarmellose sodium or crospovidone is 2.5 to 25% by weight, ferric oxide is 0.0025 to 1.5% by weight, hypromellose is 0.25 to 7.5% by weight, more preferably, present compound is 0.05 to 15% by weight, croscarmellose sodium or crospovidone is 5 to 20% by weight, ferric oxide is 0.005 to 1% by weight, hypromellose is 0.5 to 5% by weight, and titanium oxide is not contained substantially in the preparation.

When the solid preparation is a combination of present compound/croscarmellose sodium or crospovidone/ferric oxide/mannitol and the coating solid preparation wherein the coating layer, which is coated on the surface of solid preparation, is hypromellose/ferric oxide, the content of croscarmellose sodium or crospovidone, ferric oxide based on 1 part by weight of the present compound is as mentioned above. Moreover, each content per preparation is such that, usually, present compound is 0.01 to 20% by weight, croscarmellose sodium or crospovidone is 1 to 30% by weight, ferric oxide is 0.001 to 2% by weight, mannitol is 50 to 95% by weight, hypromellose is 0.1 to 10% by weight, preferably, present compound is 0.025 to 17.5% by weight, croscarmellose sodium or crospovidone is 2.5 to 25% by weight, ferric oxide is 0.0025 to 1.5% by weight, mannitol is 60 to 92.5% by weight, hypromellose is 0.25 to 7.5% by weight, more preferably, present compound is 0.05 to 15% by weight, croscarmellose sodium or crospovidone is 5 to 20% by weight, ferric oxide is 0.005 to 1% by weight, mannitol is 70 to 90% by weight, hypromellose is 0.5 to 5% by weight, and titanium oxide is not contained substantially in the preparation.

When the solid preparation is a combination of present compound/croscarmellose sodium or crospovidone/ferric oxide/mannitol/magnesium stearate and the coating solid preparation wherein the coating layer, which is coated on the surface of solid preparation, is hypromellose/ferric oxide, the content of croscarmellose sodium or crospovidone, ferric oxide based on 1 part by weight of the present compound is as mentioned above. Moreover, each content per preparation is such that, usually, present compound is 0.01 to 20% by weight, croscarmellose sodium or crospovidone is 1 to 30% by weight, ferric oxide is 0.001 to 2% by weight, mannitol is 50 to 95% by weight, magnesium stearate is 0.05 to 10% by weight, hypromellose is 0.1 to 10% by weight, preferably, present compound is 0.025 to 17.5% by weight, croscarmellose sodium or crospovidone is 2.5 to 25% by weight, ferric oxide is 0.0025 to 1.5% by weight, mannitol is 60 to 92.5% by weight, magnesium stearate is 0.075 to 7.5% by weight, hypromellose is 0.25 to 7.5% by weight, more preferably, present compound is 0.05 to 15% by weight, croscarmellose sodium or crospovidone is 5 to 20% by weight, ferric oxide is 0.005 to 1% by weight, mannitol is 70 to 90% by weight, magnesium stearate is 0.1 to 5% by weight, hypromellose is 0.5 to 5% by weight, and titanium oxide is not contained substantially in the preparation.

When the solid preparation is a combination of present compound/croscarmellose sodium or crospovidone/mannitol and the coating solid preparation wherein the coating layer, which is coated on the surface of solid preparation, is hypromellose/ferric oxide, the content of croscarmellose sodium or crospovidone, ferric oxide based on 1 part by weight of the present compound is as mentioned above. Moreover, each content per preparation is such that, usually, present compound is 0.01 to 20% by weight, croscarmellose sodium or crospovidone is 1 to 30% by weight, mannitol is 50 to 95% by weight, hypromellose is 0.1 to 10% by weight, ferric oxide is 0.001 to 2% by weight, preferably, present compound is 0.025 to 17.5% by weight, croscarmellose sodium or crospovidone is 2.5 to 25% by weight, mannitol is 60 to 92.5% by weight, hypromellose is 0.25 to 7.5% by weight, ferric oxide is 0.0025 to 1.5% by weight, more preferably, present compound is 0.05 to 15% by weight, croscarmellose sodium or crospovidone is 5 to 20% by weight, mannitol is 70 to 90% by weight, hypromellose is 0.5 to 5% by weight, ferric oxide is 0.005 to 1% by weight, and titanium oxide is not contained substantially in the preparation.

When the solid preparation is a combination of present compound/croscarmellose sodium or crospovidone/mannitol/magnesium stearate and the coating solid preparation wherein the coating layer, which is coated on the surface of solid preparation, is hypromellose/ferric oxide, the content of croscarmellose sodium or crospovidone, ferric oxide based on 1 part by weight of the present compound is as mentioned above. Moreover, each content per preparation is such that, usually, present compound is 0.01 to 20% by weight, croscarmellose sodium or crospovidone is 1 to 30% by weight, mannitol is 50 to 95% by weight, hypromellose is 0.1 to 10% by weight, ferric oxide is 0.001 to 2% by weight, preferably, present compound is 0.025 to 17.5% by weight, croscarmellose sodium or crospovidone is 2.5 to 25% by weight, mannitol is 60 to 92.5% by weight, hypromellose is 0.25 to 7.5% by weight, ferric oxide is 0.0025 to 1.5% by weight, more preferably, present compound is 0.05 to 15% by weight, croscarmellose sodium or crospovidone is 5 to 20% by weight, mannitol is 70 to 90% by weight, magnesium stearate is 0.1 to 5% by weight, hypromellose is 0.5 to 5% by weight, ferric oxide is 0.005 to 1% by weight, and titanium oxide is not contained substantially in the preparation.

When the solid preparation is a combination of present compound/ferric oxide, the content of ferric oxide based on 1 part by weight of the present compound is usually 0.001 to 1 part by weight, preferably is 0.0025 to 0.75 parts by weight, more preferably is 0.05 to 0.5 parts by weight. Moreover, each content per preparation is such that, usually, present compound is 0.01 to 20% by weight, ferric oxide is 0.001 to 2% by weight, preferably, present compound is 0.025 to 17.5% by weight, ferric oxide is 0.0025 to 1.5% by weight, more preferably, present compound is 0.05 to 15% by weight, ferric oxide is 0.005 to 1% by weight, and titanium oxide is not contained substantially in the preparation.

When the solid preparation is a combination of present compound/ferric oxide/mannitol, the content of ferric oxide based on 1 part by weight of the present compound is as mentioned above. Moreover, each content per preparation is such that, usually, present compound is 0.01 to 20% by weight, ferric oxide is 0.001 to 2% by weight, mannitol is 50 to 95% by weight, preferably, present compound is 0.025 to 17.5% by weight, ferric oxide is 0.0025 to 1.5% by weight, mannitol is 60 to 92.5% by weight, more preferably, present compound is 0.05 to 15% by weight, ferric oxide is 0.005 to 1% by weight, mannitol is 70 to 90% by weight, and titanium oxide is not contained substantially in the preparation.

When the solid preparation is a combination of present compound/ferric oxide/mannitol/magnesium stearate, the content of ferric oxide based on 1 part by weight of the present compound is as mentioned above. Moreover, each content per preparation is such that, usually, present compound is 0.01 to 20% by weight, ferric oxide is 0.001 to 2% by weight, mannitol is 50 to 95% by weight, magnesium stearate is 0.05 to 10% by weight, preferably, present compound is 0.025 to 17.5% by weight, ferric oxide is 0.0025 to 1.5% by weight, mannitol is 60 to 92.5% by weight, magnesium stearate is 0.075 to 7.5% by weight, more preferably, present compound is 0.05 to 15% by weight, ferric oxide is 0.005 to 1% by weight, mannitol is 70 to 90% by weight, magnesium stearate is 0.1 to 5% by weight, and titanium oxide is not contained substantially in the preparation.

When the solid preparation is a combination of present compound/ferric oxide and the coating solid preparation wherein the coating layer, which is coated on the surface of solid preparation, is hypromellose, the content of ferric oxide based on 1 part by weight of the present compound is as mentioned above. Moreover, each content per preparation is such that, usually, present compound is 0.01 to 20% by weight, ferric oxide is 0.001 to 2% by weight, hypromellose is 0.1 to 10 by weight, preferably, present compound is 0.025 to 17.5% by weight, ferric oxide is 0.0025 to 1.5% by weight, hypromellose is 0.25 to 7.5% by weight, more preferably, present compound is 0.05 to 15% by weight, ferric oxide is 0.005 to 1% by weight, hypromellose is 0.5 to 5% by weight, and titanium oxide is not contained substantially in the preparation.

When the solid preparation is a combination of present compound/ferric oxide/mannitol and the coating solid preparation wherein the coating layer, which is coated on the surface of solid preparation, is hypromellose, the content of ferric oxide based on 1 part by weight of the present compound is as mentioned above. Moreover, each content per preparation is such that, usually, present compound is 0.01 to 20% by weight, ferric oxide is 0.001 to 2% by weight, mannitol is 50 to 95% by weight, hypromellose is 0.1 to 10 by weight, preferably, present compound is 0.025 to 17.5% by weight, ferric oxide is 0.0025 to 1.5% by weight, mannitol is 60 to 92.5% by weight, hypromellose is 0.25 to 7.5% by weight, more preferably, present compound is 0.05 to 15% by weight, ferric oxide is 0.005 to 1% by weight, mannitol is 70 to 90% by weight, hypromellose is 0.5 to 5% by weight, and titanium oxide is not contained substantially in the preparation.

When the solid preparation is a combination of present compound/ferric oxide/mannitol/magnesium stearate and the coating solid preparation wherein the coating layer, which is coated on the surface of solid preparation, is hypromellose, the content of ferric oxide based on 1 part by weight of the present compound is as mentioned above. Moreover, each content per preparation is such that, usually, present compound is 0.01 to 20% by weight, ferric oxide is 0.001 to 2% by weight, mannitol is 50 to 95% by weight, magnesium stearate is 0.05 to 10% by weight, hypromellose is 0.1 to 10% by weight, preferably, present compound is 0.025 to 17.5% by weight, ferric oxide is 0.0025 to 1.5% by weight, mannitol is 60 to 92.5% by weight, magnesium stearate is 0.075 to 7.5% by weight, hypromellose is 0.25 to 7.5% by weight, more preferably, present compound is 0.05 to 15% by weight, ferric oxide is 0.005 to 1% by weight, mannitol is 70 to 90% by weight, magnesium stearate is 0.1 to 5% by weight, hypromellose is 0.5 to 5% by weight, and titanium oxide is not contained substantially in the preparation.

When the solid preparation is a combination of present compound and the coating solid preparation wherein the coating layer, which is coated on the surface of solid preparation, is hypromellose/ferric oxide, the content of ferric oxide based on 1 part by weight of the present compound is as mentioned above. Moreover, each content per preparation is such that, usually, present compound is 0.01 to 20% by weight, hypromellose is 0.1 to 10% by weight, ferric oxide is 0.001 to 2% by weight, preferably, present compound is 0.025 to 17.5% by weight, hypromellose is 0.25 to 7.5% by weight, ferric oxide is 0.0025 to 1.5% by weight, more preferably, present compound is 0.05 to 15% by weight, hypromellose is 0.5 to 5% by weight, ferric oxide is 0.005 to 1% by weight, and titanium oxide is not contained substantially in the preparation.

When the solid preparation is a combination of present compound/ferric oxide and the coating solid preparation wherein the coating layer, which is coated on the surface of solid preparation, is hypromellose/ferric oxide, the content of ferric oxide based on 1 part by weight of the present compound is as mentioned above. Moreover, each content per preparation is such that, usually, present compound is 0.01 to 20% by weight, ferric oxide is 0.001 to 2% by weight, hypromellose is 0.1 to 10% by weight, preferably, present compound is 0.025 to 17.5% by weight, ferric oxide is 0.0025 to 1.5% by weight, hypromellose is 0.25 to 7.5% by weight, more preferably, present compound is 0.05 to 15% by weight, ferric oxide is 0.005 to 1% by weight, hypromellose is 0.5 to 5% by weight, and titanium oxide is not contained substantially in the preparation.

When the solid preparation is a combination of present compound/ferric oxide/mannitol and the coating solid preparation wherein the coating layer, which is coated on the surface of solid preparation, is hypromellose/ferric oxide, the content of ferric oxide based on 1 part by weight of the present compound is as mentioned above. Moreover, each content per preparation is such that, usually, present compound is 0.01 to 20% by weight, ferric oxide is 0.001 to 2% by weight, mannitol is 50 to 95% by weight, hypromellose is 0.1 to 10% by weight, preferably, present compound is 0.025 to 17.5% by weight, ferric oxide is 0.0025 to 1.5% by weight, mannitol is 60 to 92.5% by weight, hypromellose is 0.25 to 7.5% by weight, more preferably, present compound is 0.05 to 15% by weight, ferric oxide is 0.005 to 1% by weight, mannitol is 70 to 90% by weight, hypromellose is 0.5 to 5% by weight, and titanium oxide is not contained substantially in the preparation.

When the solid preparation is a combination of present compound/ferric oxide/mannitol/magnesium stearate and the coating solid preparation wherein the coating layer, which is coated on the surface of solid preparation, is hypromellose/ferric oxide, the content of ferric oxide based on 1 part by weight of the present compound is as mentioned above. Moreover, each content per preparation is such that, usually, present compound is 0.01 to 20% by weight, ferric oxide is 0.001 to 2% by weight, mannitol is 50 to 95% by weight, magnesium stearate is 0.05 to 10% by weight, hypromellose is 0.1 to 10% by weight, preferably, present compound is 0.025 to 17.5% by weight, ferric oxide is 0.0025 to 1.5% by weight, mannitol is 60 to 92.5% by weight, magnesium stearate is 0.075 to 7.5% by weight, hypromellose is 0.25 to 7.5% by weight, more preferably, present compound is 0.05 to 15% by weight, ferric oxide is 0.005 to 1% by weight, mannitol is 70 to 90% by weight, magnesium stearate is 0.1 to 5% by weight, hypromellose is 0.5 to 5% by weight, and titanium oxide is not contained substantially in the preparation.

When the solid preparation is a combination of present compound/mannitol and the coating solid preparation wherein the coating layer, which is coated on the surface of solid preparation, is hypromellose/ferric oxide, the content of ferric oxide based on 1 part by weight of the present compound is as mentioned above. Moreover, each content per preparation is such that, usually, present compound is 0.01 to 20% by weight, mannitol is 50 to 95% by weight, hypromellose is 0.1 to 10% by weight, ferric oxide is 0.001 to 2% by weight, preferably, present compound is 0.025 to 17.5% by weight, mannitol is 60 to 92.5% by weight, hypromellose is 0.25 to 7.5% by weight, ferric oxide is 0.0025 to 1.5% by weight, more preferably, present compound is 0.05 to 15% by weight, mannitol is 70 to 90% by weight, hypromellose is 0.5 to 5% by weight, ferric oxide is 0.005 to 1% by weight, and titanium oxide is not contained substantially in the preparation.

When the solid preparation is a combination of present compound/mannitol/magnesium stearate and the coating solid preparation wherein the coating layer, which is coated on the surface of solid preparation, is hypromellose/ferric oxide, the content of ferric oxide based on 1 part by weight of the present compound is as mentioned above. Moreover, each content per preparation is such that, usually, present compound is 0.01 to 20% by weight, mannitol is 50 to 95% by weight, magnesium stearate is 0.05 to 10% by weight, hypromellose is 0.1 to 10% by weight, ferric oxide is 0.001 to 2% by weight, preferably, present compound is 0.025 to 17.5% by weight, mannitol is 60 to 92.5% by weight, magnesium stearate is 0.075 to 7.5% by weight, hypromellose is 0.25 to 7.5% by weight, ferric oxide is 0.0025 to 1.5% by weight, more preferably, present compound is 0.05 to 15% by weight, mannitol is 70 to 90% by weight, magnesium stearate is 0.1 to 5% by weight, hypromellose is 0.5 to 5% by weight, ferric oxide is 0.005 to 1% by weight, and titanium oxide is not contained substantially in the preparation.

The dosage form of the preparation in the present invention may be the solid preparation which is usually prescribed in the general rules for preparations of Japanese Pharmacopeia, preferably is a tablet. Examples of tablet include sustained release tablet which control dissolution rate, a chewable tablet which can be chewed in an oral cavity and an oral disintegrating tablet which disintegrates in an oral cavity in addition to a normal tablet.

The preparation of the present invention is stable against the light. The main relative substance is a ketocarboxylic acid of the compound represented by (IA). For example, when the light was irradiated on the solid preparation, the coating preparation of the present invention, the increasing amount of relative substance after light irradiation of 1,200,000 lux hour on the solid preparation, the coating solid preparation of present invention, is usually less than 0.4%, preferably less than 0.35%, more preferably less than 0.3%, compared with before light irradiation This preparation of present invention may be the solid preparation. Examples of solid preparation include granules, tablets, fine granules, pills and the like, preferably is granules or tablets.

The manufacturing method of granules in the preparation of present invention may be the method which improves the dissolution profile of present compound and decreases the amount of the relative substance, these methods do not limit the manufacturing method. For example, the preparation is manufactured by the following method. That is, the method is that the present compound and the additive agent such as disintegrator, excipient and the like are mixed, and after the mixture is manufactured, the mixture is granulated.

The granulating method of mixing powder containing the present compound, excipient, disintegrator and the like is performed by 1) extruding granulation process after kneading the mixing powder with water and the like, 2) fluidized bed granulation process spraying water and the like with the mixing powder, 3) agitation granulation process spraying water and the like with the mixing powder, 4) rolling granulation process spraying water and the like with the mixing powder, 5) fluidized bed granulation and rolling granulation process spraying water and the like with the mixing powder and the like, but the present invention is not limited by these method at all. When the granule is produced, granulation may be performed by either organic solvent except water such as ethanol, acetone, ethyl alcohol, propyl alcohol and the like, or the mixing solvent of water and organic solvent. Moreover, after producing the granules, the granules can be coated by coating agent.

The manufacturing method of tablets in the present preparation may be the method which improves the dissolution profile of present compound and decreases the amount of relative substance, these methods do not limit the manufacturing method. For example, the present preparations are manufactured by the following method. That is, the method is that 1) the present compound and the additive agent such as disintegrator, excipient and the like are mixed, and after the mixture is granulated and the granules is tableted by the tableting machine, 2) the present compound, the additive agent such as disintegrator, excipient and the like are mixed, and after the mixture is granulated and the granules is tableted by the tableting machine. As the tableting machine, single tableting machine and rotary tableting machine can be used.

When the coating agent is coated on the surface of tablet, the coating layer is formed. As the method of coating the coating agent, the tablet is coated by coating pan.

Regarding molding of the tablet, any shape can be adopted; for example, a shape of a circle, an ellipse, a sphere, a bar or a donut may be used, and further, the tablet may be multi-layer tablets and dry-coated tablets, preferably is single tablet, which is produced easily. In addition, impression such as a mark and a letter for improving discriminability, or a cleavage line for revision may be imparted.

EXAMPLES

The present invention will be explained in more detail below by way of Examples, Comparative Examples and Reference Examples, but these do not limit the present invention. Tablets obtained in Examples, Comparative Examples and Reference Examples were manufactured by the following methods and were tested for a dissolution rate, a disintegrating time of tablet and the amount of relative substance after optimal preservation.

(1) Effect of the Disintegrator (Example 1,2, Comparative Example 1,2)

To investigate the effect of disintegrator on dissolution profile and stability of products containing the present compound, manufacture tablets containing the amount of disintegrator and measure the 1) dissolution profile and 2) the increase of relative substance during stability testing. Components and composition for these tablets are shown in table 1.

a. Process for Tablet Manufacturing

The mixed powders were manufactured by mixing the amount of present compound, D-mannitol, disintegrator and magnesium stearate shown in table 1. The mixed powder was compressed by using tableting press. As a disintegrator, croscarmellose sodium (Ac-Di-Sol, manufactured by FMC Co., Ltd.), low-substituted hydroxypropylcellulose (L-HPC, manufactured by Shin-Etsu Chemical Col, Ltd.), crospovidone (kolidone CM-L, manufactured by BASF) and carmellose calcium (CMC Ca, manufactured by Gotoku Chemical Company LTD.) were used. In addition, the present compound is the p-poluenesulfonic acid salt of the compound represented by the formula (IA) and the amount of a compound represented by formula (IA) is 10 mg.

b. The Dissolution Test

In the second fluid for the dissolution test in the Japanese Pharmacopeia in the second method (JP 15), (test liquid, pH 6.8, paddle method), the dissolution rate of the compound represented by (IA) was measured at appropriate time points. In addition, the concentration of compound of the represented by (IA) was measured by an ultraviolet visible absorbance meter (8453 type, manufactured by Agilent Co. Ltd., wavelength 220 nm).

c. The Measuring Method of Relative Substances

The manufactured tablets were stored under 40° C., relative humidity 75% for a month, and the amount of total relative substances in the tablet after storage (mainly hydroxide of compound represented by formula (IA)) was measured. The measuring method of the amount of total relative substances was measured by the HPLC method (wavelength: 240 nm, column: L-column ODS (filler 5 μm, 4.6×250 mm, manufactured by chemical substance evaluation study system), column temperature: 45° C., a mobile phase: gradient method of A) 20 mmol/L phosphate buffer solution of pH 5.5/acetonitrile at HPLC mixed solution=9:1, B) acetonitrile at HPLC/methanol at HPLC mixed solution=1:1, flow rate: 1.0 mL.

d. Result

TABLE 1

|  | Example 1 | Example 2 | Comparative example 1 | Comparative example 2 |
|---|---|---|---|---|
| | | | | (Unit mg) |
| Present compound | 13.02 | 13.02 | 13.02 | 13.02 |
| D-Mannitol | 75.98 | 75.98 | 75.98 | 75.98 |
| Croscarmellose sodium | 10.00 | — | — | — |
| Crospovidone | — | 10.00 | — | — |
| Low substituted-Hydroxypropylcellulose | — | — | 10.00 | — |
| Carmellose calcium | — | — | — | 10.00 |
| Magnesium stearate | 1.00 | 1.00 | 1.00 | 1.00 |
| Sum | 100.00 | 100.00 | 100.00 | 100.00 |
| Amount of total relative substances (%) | 0.12 | — | 0.11 | 0.30 |

Figure 1:
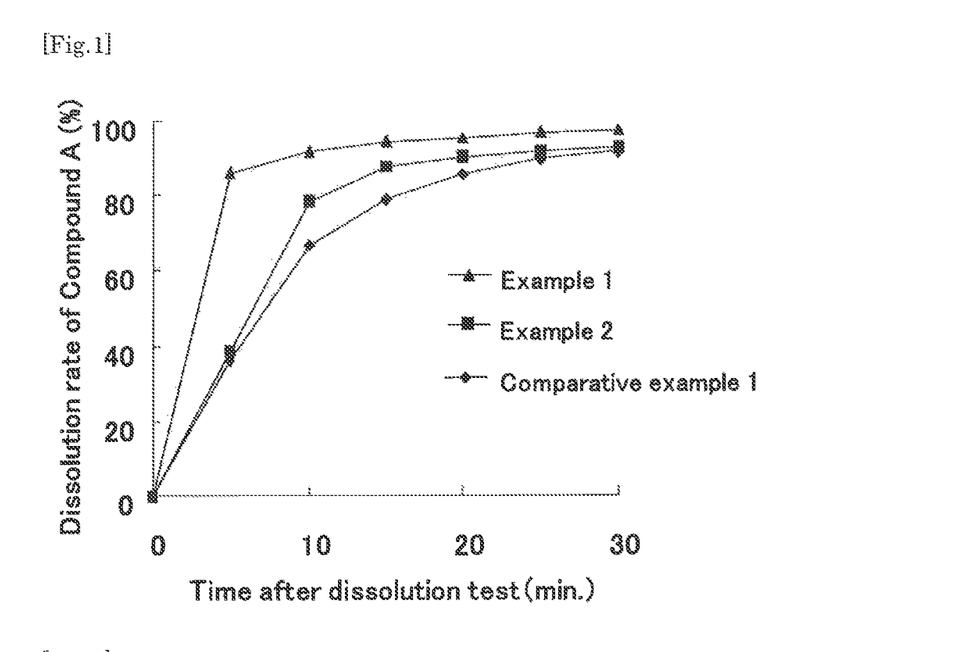
FIG. 1 Dissolution profile of the present compound in the case of changing the type of disintegrator FIG. 2 Dissolution profile of the present compound in the case of changing the content (0.1 mg) of present compound FIG. 3 Dissolution profile of the present compound in the case of changing the content (0.2 mg) of present compound

The amount of total relative substances represented by formula (IA) compound is shown in table 1. In addition, dissolution profile after the initiation of dissolution test is shown in FIG. 1. As a result, when the disintegrator was croscarmellose sodium (Example 1), the amount of total relative substances was least. Moreover, when a disintegrator is croscarmellose sodium, crospovidone, dissolution rate after 15 minutes of dissolution test was more than 85%, especially is croscarmellose sodium, dissolution rate after 5 minutes of dissolution test was more than 60%, dissolution rate after 15 minutes of dissolution test was more than 85%.

(2) Effect of the Content of Present Compound in the Preparations (Example 3)

To investigate the effect of content of present compound in the tablets, the tablets (Components and composition are shown in Table 2) were manufactured and dissolution rate was measured a. Process for Tablet Manufacturing The amount of present compound, croscarmellose sodium (Ac-Di-Sol, manufactured by FMC Co., Ltd.), D-mannitol, and magnesium stearate is shown in table 2. The amount of present compound was 0.1% by weight. The process for tablet manufacturing is as mentioned above. In addition, the present compound is the p-toluenesulfonic acid salt of the compound represented by formula (IA) and the amount of a compound represented by formula (IA) is 0.1 mg.

TABLE 2

|  | (Unit mg) Example 3 |
|---|---|
| Present compound | 0.1302 |
| D-Mannitol | 107.2698 |
| Croscarmellose sodium | 12.00 |
| Magnesium stearate | 0.60 |
| Sum | 120.00 | b. The Dissolution Test

It is as mentioned above.

c. Result

Figure 2:
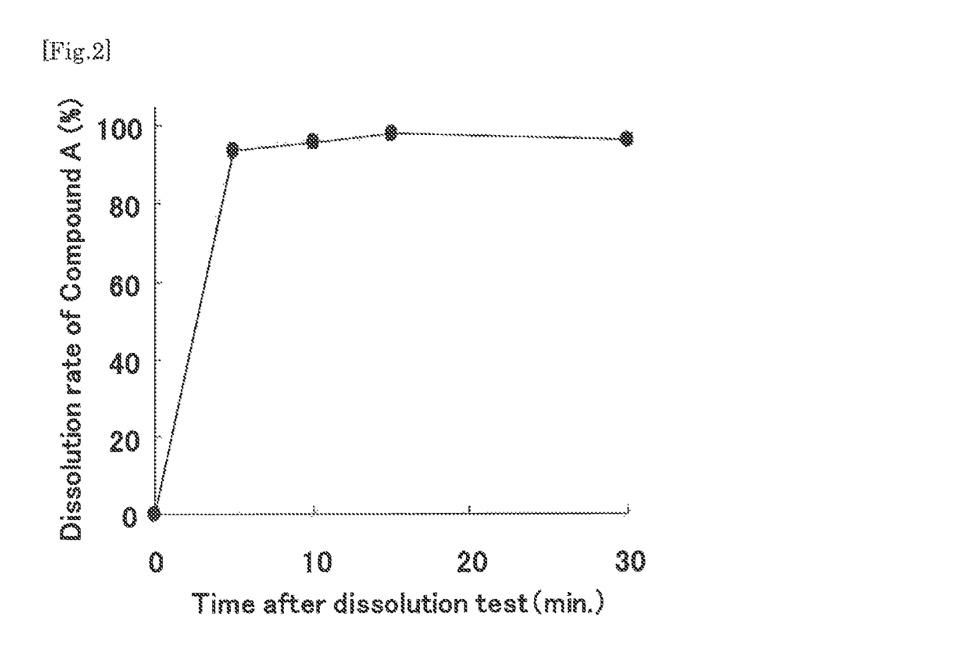

The dissolution profile of example 3 is shown in FIG. 2. The dissolution rate of the tablet of example 3 after 5 minutes of dissolution test was more than 60% together, more than 85% after 15 minutes of dissolution test, and the dissolution profile was almost same as preparation of example 1.

(3) Effect of the Pigment in the Preparations
(Reference Example 1, 2, Comparative Example 3, Example 4)

To investigate the effect of the pigment in the preparations on stability, the tablet described in Table 3 was manufactured and the amount of relative substances was measured.

a. Process for Tablet Manufacturing

The mixed powder was manufactured by sieving and mixing of present compound, D-mannitol, croscarmellose sodium and magnesium stearate. Amount of each compounds are shown in table 3. The mixed powder was compressed by single punch tableting machine, and core tablet was manufactured. After that, the coating solution containing hypromellose (hydroxypropylmethylcellulose), talc and pigment was coated to the core tablet by coating pan (48type High-Coater, manufactured by Freund Co., Ltd.) and red ferric oxide (manufactured by Kishi kasei Co., Ltd.) as pigment were used. In addition, the present compound is the p-toluenesulfonic acid salt of the compound represented by the formula (IA) and the amount of a compound represented by formula (IA) is 0.1 mg).

b. The Measuring Method of Relative Compounds

After the 1,200,000 lux hour of light was exposed to the manufactured tablet, the increased amount of relative substances (mainly ketocarbonate of compound represented by formula (IA)) was measured. The measuring method of the amount of total relative substance was measured by the HPLC method (wavelength: 240 nm, L-column ODS (filter 5 μm, 4.6×250 mm, manufactured by chemical substance evaluation study system), column temperature: 45° C., a mobile phase: The gradient method of A) 20 mmol/L phosphate buffer solution of pH 5.5/acetonitrile at HPLC mixed solution=9:1, B) acetonitrile at HPLC/methanol at HPLC mixed solution=1:1, flow rate: 1.0 mL. In addition, the total amount of relative substance before irradiation of light was 0.08%.

c. Result

TABLE 3

|  | Reference example 1 | Reference example 2 |
|---|---|---|
| | | (Unit mg) |
| Present compound | 0.1302 | 0.1302 |
| D-Mannitol | 88.8698 | 88.8698 |

TABLE 3-continued

| | | |
|---|---|---|
| Croscarmellose sodium | 10.00 | 10.00 |
| Magnesium stearate | 1.00 | 1.00 |
| Sum of Core Tablet | 100.00 | 100.00 |
| Hypromellose | — | 2.8 |
| Talc | — | 1.2 |
| Titanium oxide | — | — |
| Red ferric oxide | — | — |
| Sum | 100.0 | 104.0 |
| The increased amount of relative substances after 1,200,000 lux hour exposure (%) | 0.27 | 0.22 |

| | Comparative example 3 | Example 4 |
|---|---|---|
| Present compound | 0.1302 | 0.1302 |
| D-mannitol | 88.8698 | 88.8698 |
| Croscarmellose sodium | 10.00 | 10.00 |
| Magnesium stearate | 1.00 | 1.00 |
| Sum of Core Tablet | 100.00 | 100.00 |
| Hypromellose | 2.8 | 2.8 |
| Talc | 0.32 | 1.2 |
| Titanium oxide | 0.88 | — |
| Red ferric oxide | — | 0.04 |
| Sum | 104.0 | 104.04 |
| The increased amount of relative substances after 1,200,000 lux hour exposure (%) | 1.46 | 0.18 |

As shown in Table 3, the increased amount of relative substances was not almost changed in the reference example 2, which was coated with hypromellose and talc without pigment compared with that in reference example 1. However, the amount of relative substances of comparative example 3 which is coated with hypromellose, talc and titanium oxide as pigment increased remarkably. On the other hand, when a red ferric oxide was coated to example 4, the amount of relative substances in example 4 was decreased, compared with that in comparative example 3, reference example 1 without a coating layer and reference example 2 without a pigment.

(3) Effect of the Content of the Present Compound in the Preparations (Example 5)

To investigate the effect of the content of present compound in the preparations on dissolution, the tablet described in Table 4 was manufactured and the dissolution rate was measured.

a. Process for Tablet Manufacturing

The present compound, D-mannitol, croscarmellose sodium and magnesium stearate of amount shown in table 4 was sieved and mixed and the mixed powder is manufactured. The mixed powder was compressed by single tableting machine and core tablet was manufactured. After that, the coating solution containing hypromellose (hydroxypropylmethylcellulose), talc and pigment was coated to the core tablet by coating pan (48type High-Coater, manufactured by Freund Co., Ltd.). The red ferric oxide (manufactured by Kishi kasei Col, Ltd.) as pigment were used. In addition, the present compound is the p-toluenesulfonic acid salt of the compound represented by the formula (IA) and the amount of a compound represented by formula (IA) is 0.2 mg.

TABLE 4

| | (Unit mg) Example 5 |
|---|---|
| Present compound | 0.2604 |
| D-mannitol | 107.1396 |
| Croscarmellose sodium | 12.00 |
| Magnesium stearate | 0.60 |
| Sum of Core Tablet | 120.00 |
| Hypromellose | 3.2 |
| Talc | 1.30 |
| Red ferric oxide | 0.05 |
| Sum | 124.55 | b. The Dissolution Test

It is as mentioned above.

c. Result

Figure 3:
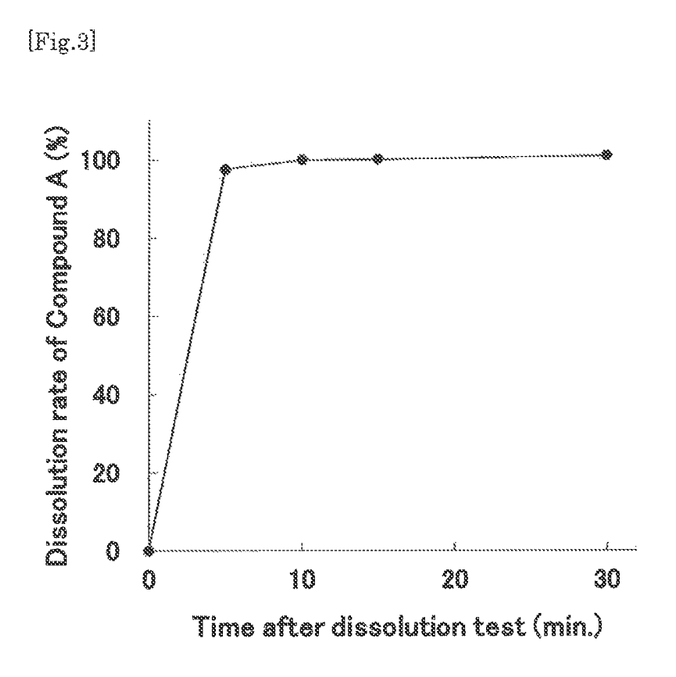

The dissolution profile of example 5 is shown in FIG. 3. The dissolution rate of example 5 tablet after 5 minutes of dissolution test was more than 60% together, more than 85% after 15 minutes of dissolution test, and the dissolution profile was almost same as that of example 1 tablet.

AVAILABILITY IN THE INDUSTRY

When Croscarmellose sodium as a disintegrator was used, the dissolution profile of 6,7-unsaturation-7-carbamoyl morphinan derivative can be improved. Furthermore, when the ferric oxide was used without using titanium oxide as a pigment, the amount of relative substances was decreased, and the identification of the tablet was enabled.

The invention claimed is:

1. A solid preparation, which comprises about 0.2604 mg of a p-toluenesulfonic acid salt of a compound represented by formula (IA), (IA)

as an active ingredient, about 12 mg of croscarmellose sodium, about 0.05 mg ferric oxide, about 107.1396 mg D-mannitol, about 0.60 mg magnesium stearate, about 3.2 mg hypromellose, and about 1.30 mg talc,
  wherein the dissolution rate of the compound represented by formula (IA) is more than 85% after 15 minutes of the test initiation in the second liquid of the dissolution test using the paddle method of the 15$^{th}$ edition of the Japanese Pharmacopeia, and
  wherein the solid preparation comprises less than 0.2% of a hydroxide or ketocarboxylic acid of the compound represented by formula (IA) as measured by HPLC after storage at 40° C. and 75% relative humidity for one month.

2. The solid preparation according to claim 1, which further comprises one or more pigments selected from the group consisting of tar dye and natural dye, and does not substantially contain titanium oxide.

3. The solid preparation according to claim 1, wherein the ferric oxide, the hypromellose and the talc are in a coating layer on a surface of the solid preparation.

4. The solid preparation according to claim 3, wherein the coating layer further comprises one or more pigments selected from the group consisting of tar dye and natural dye and the coating layer does not substantially contain titanium oxide.

5. The solid preparation according to claim 3, wherein the ferric oxide is at least one selected from the group consisting of iron sesquioxide and yellow iron sesquioxide.

6. The solid preparation according to claim 1, wherein the ferric oxide is at least one selected from the group consisting of iron sesquioxide and yellow iron sesquioxide.

7. The solid preparation according to claim 1, wherein the preparation is a tablet or a granule.

8. A coated solid preparation, which comprises about 0.21% of a p-toluenesulfonic acid salt of a compound represented by formula (IA),

(IA)

as an active ingredient, about 9.63% croscarmellose sodium, about 0.04% ferric oxide, about 86.02% D-mannitol, about 0.48% magnesium stearate, about 2.57% hypromellose, and about 1.04% talc by weight of the solid preparation, and a coating layer,
wherein the coating layer contains the ferric oxide, the hypromellose and the talc, and does not substantially contain titanium oxide,
wherein an increased amount of a hydroxide or ketocarboxylic acid of the compound represented by formula (IA) after light irradiation of 1,200,000 lux hour in the coated solid preparation is less than 0.4% as measured by HPLC compared to before the light irradiation.

9. The solid preparation according to claim 8, wherein the preparation is a tablet or a granule.

10. The solid preparation according to claim 8, wherein the ferric oxide is at least one selected from the group consisting of iron sesquioxide and yellow iron sesquioxide.

11. A solid preparation, which comprises about 0.21% of a p-toluenesulfonic acid salt of a compound represented by formula (IA), (IA)

as an active ingredient, about 9.63% of croscarmellose sodium, about 0.04% ferric oxide, about 86.02% D-mannitol, about 0.48% magnesium stearate, about 2.57% hypromellose, and about 1.04% talc by weight of the solid preparation,
wherein the dissolution rate of the compound represented by formula (IA) is more than 85% after 15 minutes of the test initiation in the second liquid of the dissolution test using the paddle method of the $15^{th}$ edition of the Japanese Pharmacopeia, and
wherein the solid preparation comprises less than 0.2% of a hydroxide or ketocarboxylic acid of the compound represented by formula (IA) as measured by HPLC after storage at 40° C. and 75% relative humidity for one month.

12. The solid preparation according to claim 11, wherein the preparation is a tablet or a granule.

13. The solid preparation according to claim 11, wherein the ferric oxide is at least one selected from the group consisting of iron sesquioxide and yellow iron sesquioxide.

* * * * *